(12) United States Patent
Furlong et al.

(10) Patent No.: US 6,521,189 B1
(45) Date of Patent: Feb. 18, 2003

(54) COMBINED LABORATORY CONDENSOR AND VESSEL CONNECTOR

(75) Inventors: Brian Henry Furlong, Hertford (GB); Clive Adrian Smith, Hertford (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 09/485,314

(22) PCT Filed: Aug. 10, 1998

(86) PCT No.: PCT/EP98/05118
§ 371 (c)(1),
(2), (4) Date: Apr. 24, 2000

(87) PCT Pub. No.: WO99/08767
PCT Pub. Date: Feb. 25, 1999

(30) Foreign Application Priority Data

Aug. 15, 1997 (GB) .............................................. 9717229

(51) Int. Cl.[7] .............................................. B01L 11/00
(52) U.S. Cl. .............................. 422/101; 422/99; 165/73
(58) Field of Search ........................... 422/99, 61, 101; 202/83, 152, 163; 165/72, 75, 74, 110, 73

(56) References Cited

U.S. PATENT DOCUMENTS

| | | | | |
|---|---|---|---|---|
| 3,098,800 A | * | 7/1963 | Moran et al. | 202/170 |
| 4,333,523 A | * | 6/1982 | Hartzler | 165/73 |
| 4,678,028 A | * | 7/1987 | Conant et al. | 165/72 |
| 5,080,695 A | * | 1/1992 | Kassarjian | 55/53 |
| 5,114,567 A | | 5/1992 | DiFoggio | |
| 5,398,806 A | * | 3/1995 | Quinn | 202/83 |
| 5,417,924 A | | 5/1995 | Di-Maetino et al. | |

* cited by examiner

*Primary Examiner*—Jill Warden
*Assistant Examiner*—Brian Sines
(74) *Attorney, Agent, or Firm*—James M. Kanagy; Charles M. Kinzig

(57) ABSTRACT

A combined laboratory condenser and vessel connector having a conduit with an inlet/outlet adjacent its upper end with a condenser jacket around the lower part of the conduit, an upper part of the jacket formed into or provided with a connector to enable the apparatus to be mated with a vessel with at least part of the jacket extending into the vessel. The device is useful in chemical laboratory operations.

15 Claims, 1 Drawing Sheet

COMBINED LABORATORY CONDENSOR AND VESSEL CONNECTOR

Figure 1:
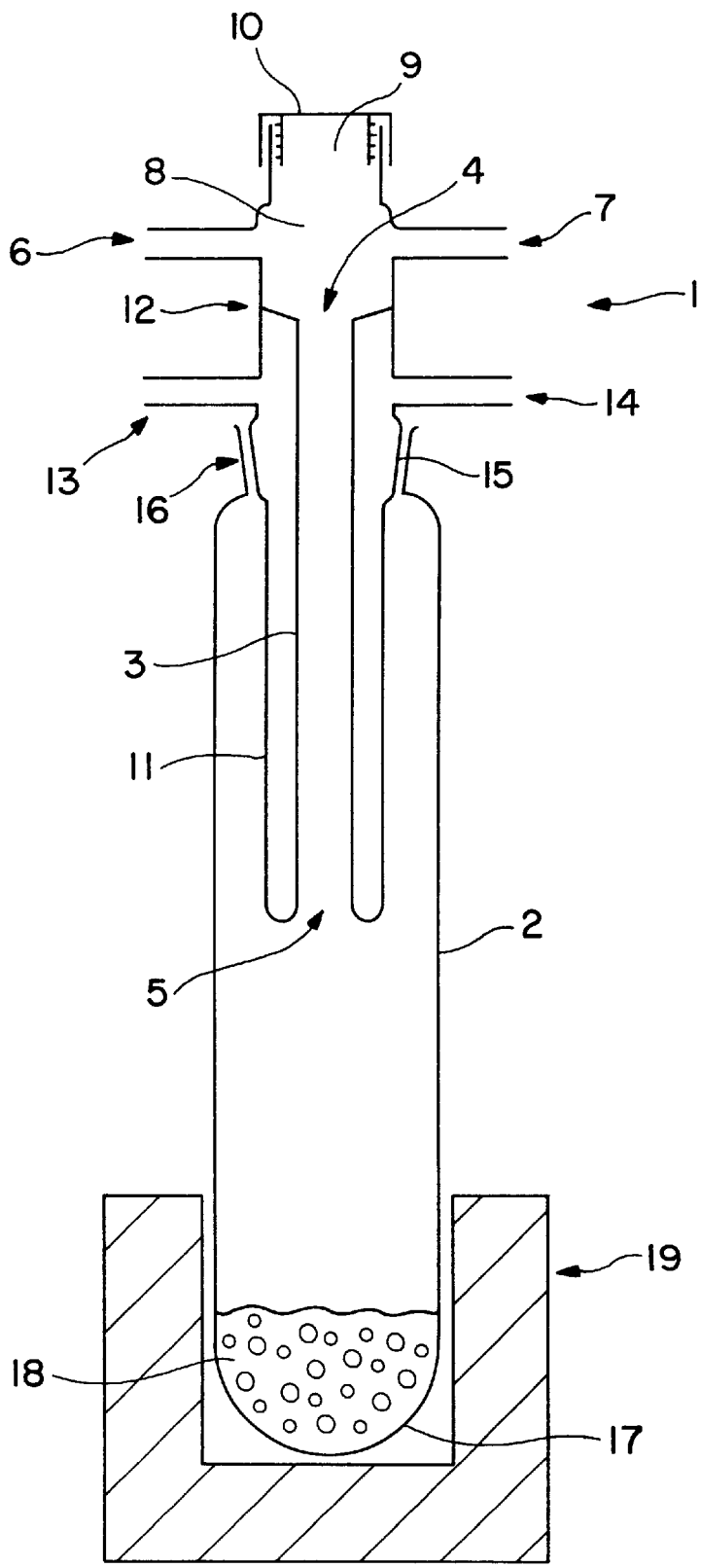

This invention relates to a novel device, being a combined gas inlet and cold finger condenser suitable for use in connection with chemical laboratory apparatus.

Chemical apparatus for performing laboratory chemical reactions is becoming increasingly complex as the number of functions that laboratory apparatus is required to perform increases. Multi-necked vessels enable a multitude of devices e.g. stirrers, condensers, gas inlets to be connected to the vessel. but at the cost of increased complexity and crowding of the devices. Numerous types of connector for laboratory apparatus such as flasks, reaction vessels etc. are known from the literature of classical chemical synthesis, and the patent literature also discloses some connectors of this general type. For example U.S. Pat. No. 5,398,806, U.S. Pat. No. 4,333,523 and U.S. Pat. No. 3,098,800 disclose various types of condensers and distillation apparatus.

It is an object of this invention to provide an improved device which can engage with a standard neck fitting, e.g. a ground glass neck connection, of a laboratory vessel and by means of which a number of laboratory operations can be performed. In particular it is an object of this invention to provide an apparatus of this type which is advantageous for use in automated laboratory reactors, e.g. inter alia having the advantages of compactness, versatility and use in a multiplicity of functions.

According to this invention an apparatus is provided being a combined condenser and vessel connector parn, comprising:

a tubular conduit extending from an upper open end to a lower open end, with at least one inlet I outlet adjacent the upper end of the conduit, a condenser in the form of a jacket around the lower part of the conduit and extending upwardly toward the upper end of the conduit, the upper part of the condenser being provided with a cooling fluid inlet and outlet, an upper part of the jacket, between the cooling fluid inlet and outlet and the lower end, being formed into or provided with a connector to enable the apparatus to be mated with a corresponding matin, connector on the mouth of a vessel to thereby enable the apparatus to be sealingly connected with the vessel with at least part of the jacket extending into the vessel.

In this description the terms "upper" and "lower" and derived terms are used relative to the normal in-use orientation of a vessel to which the apparatus is mated, with the mouth of the vessel upward.

In an alternative description the invention provides an apparatus comprising:

a condenser in the form of a conduit having an upper open end and a lower open end, at least part of the conduit being surrounded by a jacket suitable for the containment and flow therethrough of a cooling fluid, the jacket being provided with an inlet and an outlet for said cooling fluid, a part of said jacket between the inlet or outlet and the lower open end of the conduit being formed into or provided with a connector to enable the apparatus to be mated with a corresponding mating connector on the mouth of a vessel to thereby enable the apparatus to be sealingly connected with the vessel, an upper part of the conduit being provided with at least one inlet and outlet in communication with the conduit by means of which substances may be introduced or removed from a vessel with which the apparatus is sealingly mated.

Preferably in this embodiment too at least part of the jacket extends into the vessel when the apparatus is mated with the vessel.

In another alternative description this invention provides an apparatus comprising:

a tubular conduit extending from an upper open end to a lower open end, a condenser in the form of a jacket around the conduit, the condenser being provided with a cooling fluid inlet and outlet, part of the jacket, between the cooling fluid inlet or outlet and the lower end, being formed into or provided with a connector to enable the apparatus to be mated with a corresponding mating connector on the mouth of a vessel to thereby enable the apparatus to be sealingly connected with the vessel with at least part of the jacket extending into the vessel.

For example in all of these embodiments at least 25%, preferably at least 50% of the lower part of the jacket extends into the vessel, thereby comprising an effective double surfaced condenser exposed to the interior of the vessel.

Preferably the entire apparatus is made of glass, preferably integrally, although other materials such as metals may be used for part of or the entire apparatus for particular applications. The making of such an apparatus is well within the competence of a skilled glass blower using the types of glass normally used for laboratory glassware. If the apparatus or parts of it are made of metals these should be inert to the substances with which the apparatus is to come into contact.

Alternatively the apparatus may be in two or more parts, which may fit together using appropriate joints, for example of a type known in the field of laboratory apparatus.

The one or more inlet or outlet may be used in alternative roles each as respectively an inlet or an outlet, e.g. for a gas or for the application of a vacuum. Preferably there are two inlet I outlets so that in use one may be used as an inlet and the other as an outlet, and both may be suitable for the introduction of a flow of gas in via the inlet, and if the outlet is present, the outlet being suitable for the exit of the flow of gas. The said inlet and outlet may be provided with control valves to open and close off a flow of gas through them.

Preferably the inlet and/or outlet are adjacent the upper end of the tubular conduit.

Preferably at or adjacent the upper end of the tubular conduit there is also a mouth opening which opens generally in axial line with the tubular conduit. Such a mouth opening may comprise a standard connector for laboratory apparatus, e.g. a ground glass connector, a septum cap connector, screw thread or flange connector etc. Suitable types of connector for any application will be apparent to those skilled in the art. The mouth opening may be of suitable dimensions to allow a stirrer, sampler, syringe, thermometer, probe or other device etc. to be inserted down through the conduit and into a vessel with which the apparatus is mated.

Preferably at the upper end of the conduit there is a chamber, in integral communication with the conduit, and into which the inlet and if present the optional outlet, and if present the optional mouth opening open. For example the upper part of the conduit may widen to define such a chamber, and the inlet and if present the optional outlet, and if present the optional mouth opening may open into this chamber.

Preferably the apparatus is substantially linear, along an axis which passes through the conduit, with the jacket surrounding the conduit coaxially. In such a construction the mouth opening may open in line with, e.g. coaxially with, the axis of the conduit, and the inlet and/or outlet may open into side walls of the conduit or into side walls of the above-mentioned chamber.

The connector with which the jacket is provided or formed may suitably be provided by making the outside of the jacket in the form of a standard laboratory fitting, e.g. as a tapering ground glass male or female joint or a flange joint etc. Suitable other types of connector will be apparent to those skilled in the art, e.g. a glass ball joint, screw threaded connection or a flange connection etc. Below this joint the condenser may be of narrow dimensions to enable the condenser to be inserted through a corresponding mating joint in the mouth opening of a vessel, and for the connector on the apparatus to connect with the mouth of the vessel.

The apparatus may be used for refluxing whilst introducing a flow of a gas in through the inlet, and the gas may then flow through the conduit and into a vessel to which the vessel is connected, or out through the optional outlet or the optional mouth opening.

The apparatus is suitable for use in connection with laboratory vessels of all types having suitable connections and dimensions. The apparatus of this invention is compact and is particularly suited for use with known types of automated, e.g. robot, laboratory equipment.

The invention also provides a method of use of an apparatus according to any preceding claim for refluxing whilst introducing a flow of a gas in through the inlet.

An advantage of the apparatus of the invention is its condensing ability. When a vessel is connected to the apparatus, hot vapour from inside the vessel can only gain access to the exterior via the condenser, i.e. it is not possible for hot vapour from the vessel to leave the apparatus without coming into contact with the cooled surfaces of the condenser.

The apparatus and method of the invention will now be described by way of example only with reference to FIG. 1, which shows a longitudinal section through the apparatus of the invention, in use, connected to a reaction vessel.

Referring to FIG. 1, an apparatus of the invention is shown overall 1, connected to a vessel 2. The apparatus 1 is integrally made of glass.

The apparatus 1 comprises a linear cylindrical tubular conduit 3 which extends between an upper open end 4 and a lower open end 5, these directions being defined with the vessel to which the apparatus is mated being in its normal orientation with its mouth upward. Adjacent to the upper open end 4 is an inlet tube 6, and there is, in the embodiment shown, also an outlet tube 7 both suitable for use as gas inlets and/or outlets, either or both of which may be provided with valves (not shown). In an alternative construction the outlet 7 may be absent and only the inlet/outlet 6 may be present. Adjacent to the upper open end 4 is a chamber 8 in integral communication with the conduit 3, and into which the inlet 6 and outlet 7 lead.

Adjacent to the open upper end 4 there is also a mouth opening 9 in the form of a connector for, and into which is fitted, a septum cap 10. A suitable connector for a septum cap comprises a smooth glass tube. The mouth opening 9 may comprise a connection for other devices e.g. for sampling, monitoring or addition of substances which could be inserted into mouth opening 9, for example the mouth opening 9 could comprise a standard laboratory ground glass connection. The mouth opening 9 opens into chamber 8, and opens generally in line with the long axis of the conduit 3.

Around the lower part of the conduit 3 is a condenser in the form of a cylindrical glass jacket 11 terminating and integrally joined to conduit 3 at its lower end 5, extending upwards towards the upper end 4 of the conduit, and concentrically surrounding the conduit 3. The conduit 3 could in alternative embodiments extend below the lowest part of the jacket 11. At its upper end the jacket 11 is integrally joined to the lower rim of the chamber 8 at 12. Alternatively the upper end of the jacket 11 could be joined to the conduit 3 below the chamber 8.

Adjacent the upper end of the jacket 11 is a cooling fluid inlet 13 and a cooling fluid outlet 14. Below the inlet 13 and outlet 14 the outer surface of the jacket 11 is formed into a connector being a tapering ground glass joint 15 capable of engaging with a corresponding female joint 16 on vessel 2 or other apparatus. It will be apparent to those skilled in the art how alternative types of connector 15 may be provided using techniques common in the field of glassblowing etc., e.g. a flange connector.

The overall length of the apparatus as shown is ca 12.5 cm, suitable for the joint 15 to be a CNB19 size fitting, but obviously size can be varied to suit the application. Instead of the joint 15 the jacket may be provided with for example an external flange or other kind of mating fitting so that the apparatus may mate with a corresponding fitting on a vessel 2.

In use, as shown in FIG. 1, the apparatus 1 is inserted into a vessel 2 having a ground glass mouth opening 16 sealingly engageable with the joint 15 on the jacket 11, the relative dimensions of the vessel 2 and apparatus 1 being selected such that the lower end 5 of the conduit 3 is at a convenient height above the bottom 17 of vessel 2, and above the surface of contents 18 in the vessel 2. The vessel 2 is for convenience shown as being a round bottomed tubular vessel, but obviously other types of vessel could be used, e.g. a flat bottomed tubular vessel or a multi-necked flask etc.

A reaction mixture 18 in the vessel 2 may be heated. The condenser jacket 11 extends into the vessel 2 so its outer surface is exposed to the hot vapour within the vessel 2. A flow of cold water (or other cooling fluid) is passed through the condenser 11 via the inlet 13 and outlet 14, and causes liquid vapour to condense on the outside of the jacket 1 of the condenser, and also within the conduit 3. Consequently condensation of the vapour occurs both within the vessel 2 and up the conduit 3, including the upper parts of the conduit 3 external to the vessel. At the same time a current of gas, which may be a reactive or an inert gas may be passed into the apparatus via inlet 6, and exit via outlet 7. Alternatively if outlet 7 is not present or is closed off the gas may exit via a gas bubbler (e.g. a Firestone valve), a side arm or another neck (not shown) of the vessel 2. Other ways of introducing gas into the apparatus 1 and vessel 2 will be apparent to those skilled in the art. Reagents may be introduced, or samples may be withdrawn, via the septum cap 10. Alternatively, if the conduit is suitably sized, stirrers, thermometers and other equipment or instruments may be inserted down the conduit 3 into the vessel 2 or reaction mixture 18. The reaction mixture 18 may conveniently be heated by heater block 19, which may include a stirrer (not shown). The inlet 6 may be connected via suitable valves (not shown) to a manifold block (not shown) by means of which the apparatus 1 and vessel 2 connected to it may be evacuated or a gas introduced.

We claim:

1. An apparatus being a combined condenser and vessel connector part, comprising:

a tubular conduit extending from an upper open end to a lower open end, at the upper end of the tubular conduit there being a mouth opening which opens generally in line with the upper end-lower end axial line of the conduit, with at least one inlet into the conduit or outlet out of the conduit adjacent the upper end of the conduit in addition to the mouth opening, a condenser in the form of a jacket around the lower part of the conduit and extending upwardly toward the upper end of the conduit, the upper part of the condenser being provided with a cooling fluid inlet and outlet, whereby a flow of cooling fluid may be directed through said jacket to cause vapour inside the conduit to be condensed to a liquid, an upper part of the jacket, between the cooling fluid inlet and outlet and the lower end, being formed into or provided with a connector to enable the apparatus to be mated with a corresponding mating connector on the mouth of a vessel, at least part of the jacket extending below the connector to thereby enable the apparatus to be sealingly connected with the vessel with at least part of the jacket extending into the vessel, so that vapour in the vessel is condensed on the outside of the jacket.

2. An apparatus comprising:

a condenser in the form of a tubular conduit having an upper open end and a lower open end, at least part of the conduit being surrounded by a jacket for the containment and flow therethrough of a cooling fluid, the jacket being provided with an inlet and an outlet for said cooling fluid, whereby a flow of cooling fluid may be directed through said jacket to cause vapour inside the conduit to be condensed to a liquid, a part of said jacket between the inlet or outlet and the lower open end of the conduit being formed into or provided with a connector to enable the apparatus to be mated with a corresponding mating connector on the mouth of a vessel to thereby enable the apparatus to be sealingly connected with the vessel, at least part of the jacket extending below the connector to thereby enable the apparatus to be sealingly connected with the vessel with at least part of the jacket extending into the vessel, so that vapour in the vessel is condensed on the outside of the jacket, an upper part of the conduit being provided with at least one inlet and outlet in communication with the conduit, at the upper end of the tubular conduit there being a mouth opening which opens generally in line with the upper end-lower end axial line of the conduit, in addition to said inlet and outlet.

3. An apparatus according to claim 1 integrally made of glass.

4. An apparatus according to claim 1 wherein the one or more inlet/outlet may be used in alternative roles each as respectively an inlet or an outlet for a gas or for the application of a vacuum.

5. An apparatus according to claim 1 wherein adjacent the upper end of the tubular conduit there are two inlet/outlets, so that in use one may be used as an inlet and the other as an outlet.

6. An apparatus according to claim 1 wherein the mouth opening comprises a standard connector for laboratory apparatus.

7. An apparatus according to claim 1 wherein at the upper end of the conduit there is a chamber, in integral communication with the conduit, and into which the inlet and if present the optional outlet, and if present the optional mouth opening open.

8. An apparatus comprising:

a tubular conduit extending from an upper open end to a lower open end, a condenser in the form of a jacket around the conduit, the condenser being provided with a cooling fluid inlet and outlet, whereby a flow of cooling fluid may be directed through said jacket to cause vapour inside the conduit to be condensed to a liquid, part of the jacket, between the cooling fluid inlet or outlet and the lower end, being formed into or provided with a connector to enable the apparatus to be mated with a corresponding mating connector on the mouth of a vessel to thereby enable the apparatus to be sealingly connected with the vessel with at least part of the jacket extending into the vessel so that vapour in the vessel is condensed on the outside of the jacket.

9. An apparatus according to claim 1 being substantially linear, along an axis which passes through the conduit, with the jacket surrounding the conduit coaxially.

10. An apparatus according to claim 1 wherein the upper part of the jacket, between the cooling fluid inlet and outlet and the lower end, is formed into or provided with a connector by making the outside of the jacket in the form of a laboratory glassware fitting.

11. An apparatus according to claim 1 wherein at least 25% of the jacket extends below the connector.

12. An apparatus according to claim 11 wherein at least 50% of the jacket extends below the connector.

13. An apparatus comprising:

a substantially linear tubular conduit having a lower open end and an upper open end, a chamber having an upper end and a lower end, the lower end of the chamber being adjacent to and in integral communication with the conduit at the upper end of the conduit, the chamber having a mouth opening at its upper end and which opens generally in axial line with the tubular conduit, at least one inlet/outlet opening into the chamber, additional to said mouth opening, at least part of the conduit being surrounded by a condenser in the form of a jacket for the containment and flow therethrough of a cooling fluid, the jacket being provided with an inlet and an outlet for said cooling fluid, whereby a flow of cooling fluid may be directed through said jacket to cause vapour inside the conduit to be condensed to a liquid, a part of the outer surface of the jacket being a connector in the form of a tapering ground glass male laboratory fitting connectable to a corresponding female fitting of a vessel, the cooling fluid inlet and outlet being located between the connector and the inlet/outlet, the jacket extending below the connector so as to extend into said vessel when the apparatus is connected to said vessel, so that vapour in the vessel is condensed on the outside of the jacket.

the apparatus being made integrally of glass.

14. An apparatus according to claim 14 and wherein at least 25% of the jacket extends below the connector so as to extend into said vessel when the apparatus is connected to said vessel.

15. An apparatus according to claim 14 and wherein at least 50% of the jacket extends below the connector so as to extend into said vessel when the apparatus is connected to said vessel.

* * * * *